(12) United States Patent
Sun et al.

(10) Patent No.: US 11,890,602 B2
(45) Date of Patent: Feb. 6, 2024

(54) APPLICATION OF THE IONIC IRON (III) COMPLEX AS CATALYST IN PREPARATION OF BENZYLAMINE COMPOUND

(71) Applicant: SOOCHOW UNIVERSITY, Suzhou (CN)

(72) Inventors: Hongmei Sun, Suzhou (CN); Ruipeng Li, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 537 days.

(21) Appl. No.: 17/239,496

(22) Filed: Apr. 23, 2021

(65) Prior Publication Data

US 2021/0237044 A1    Aug. 5, 2021

Related U.S. Application Data

(63) Continuation of application No. PCT/CN2018/112510, filed on Oct. 29, 2018.

(51) Int. Cl.
| | | |
|---|---|---|
| *C07C 253/30* | (2006.01) | |
| *B01J 31/22* | (2006.01) | |
| *B01J 37/08* | (2006.01) | |
| *B01J 37/12* | (2006.01) | |

(52) U.S. Cl.
CPC ............... *B01J 31/22* (2013.01); *B01J 37/08* (2013.01); *B01J 37/12* (2013.01)

(58) Field of Classification Search
None
See application file for complete search history.

(56) References Cited

FOREIGN PATENT DOCUMENTS

| CN | 103408433 A | | 11/2013 | |
|---|---|---|---|---|
| CN | 105481695 A | | 4/2016 | |
| CN | 107311890 A | * | 11/2017 | .......... B01J 31/1815 |
| CN | 107311890 A | | 11/2017 | |
| CN | 107935860 A | | 4/2018 | |
| CN | 109232265 A | | 1/2019 | |
| CN | 109320434 A | | 2/2019 | |

* cited by examiner

*Primary Examiner* — Yun Qian
(74) *Attorney, Agent, or Firm* — SZDC Law PC

(57) ABSTRACT

Disclosed is an application of an ionic iron (III) complex as a catalyst in preparation of a benzylamine compound, that is, an ionic iron (III) complex having a molecular formula of [(RNCHCHNR)CH][FeBr$_4$] (R is tert-butyl) and containing 1,3-di-tert-butyl imidazolium cation is used as a catalyst, di-tert-butyl peroxide is used as an oxidizing agent, and a benzylamine compound is synthesized by oxidation reaction of a toluene/ethylbenzene compound with an aromatic amine. The present invention has a wide application range, and is applicable not only to a toluene compound containing a benzylic primary carbon-hydrogen bond but also to an ethylbenzene compound containing a benzyl secondary carbon-hydrogen bond. This is the first example of the preparation of a benzylamine compound by oxidation reaction of a toluene/ethylbenzene compound and an aromatic amine by an iron-based catalyst.

1 Claim, No Drawings

APPLICATION OF THE IONIC IRON (III) COMPLEX AS CATALYST IN PREPARATION OF BENZYLAMINE COMPOUND

This application is a Continuation Application of PCT/CN2018/112510, filed on Oct. 29, 2018, which is incorporated by reference for all purposes as if fully set forth herein.

TECHNICAL FIELD

The invention relates to the technical field of organic synthesis, and particularly relates to the application of an ionic iron (III) complex as a catalyst in preparing a benzylamine compound.

BACKGROUND TECHNIQUE

As a key backbone structure, benzylamine compounds widely exist in natural products, pesticides, polymers and drug molecules. Traditional synthesis of such compounds requires the use of pre-functionalized substrates, such as halogenated hydrocarbons, through the Buchwald-Hartwig (Buchwald-Hartwig) cross-coupling reaction (see: J. F. Hartwig, Acc. Chem. Res., 2008, 41, 1534). This method has the disadvantages of poor atomic economy and emission of halides that cause serious pollution to the environment. Therefore, the development of new methods for the synthesis of benzylamine compounds is of great practical value.

In recent years, the transition metal-catalyzed carbon-hydrogen bond oxidation reaction to construct carbon-nitrogen bonds has become a new method for synthesizing amine compounds. This method avoids the use of halogenated hydrocarbons and has better atomic economy and environmentally friendly. However, there are very few reports concerning the oxidation reaction of the carbon-hydrogen bond in the benzylic position, and the disclosed copper catalyst system is only applicable to the substrate containing the secondary carbon-hydrogen bond in the benzylic position.

In the past ten years, iron-based catalysts have been rapidly developed due to their advantages, such as lower price and wide availability, low toxicity or non-toxicity, and good biocompatibility. But there are no literature reports on the oxidation of carbon-hydrogen bonds at the benzyl site involving iron catalysts. Therefore, the development of high-efficiency iron-based catalysts and the construction of benzylamine compounds through the reaction of benzene compounds and aromatic amines are in line with the development requirements of green chemistry, and are also highly innovative and valuable in application.

Technical Problem

The object of the present invention is to provide an application of the ionic iron (III) complex as a catalyst in preparing a benzylamine compound. It is a new method for the synthesis of the benzylamine compound, that is, using an ionic iron (III) complex with the molecular formula of [($^t$BuNCHCHN$^t$Bu)CH][FeBr$_4$] containing 1,3-di-tert-butylimidazole cation as a catalyst, di-tert-butyl peroxide as an oxidizing agent, reacting a toluene/ethylbenzene compound with an arylamine to synthesize the benzylamine compound. [($^t$BuNCHCHN$^t$Bu)CH][FeBr$_4$] is an iron (III) complex with a clear structure that is simple, easy to obtain, and stable in air.

Technical Solution

In order to achieve the above-mentioned object of the invention, the technical solution adopted by the present invention is:

An application of the ionic iron (III) complex as a catalyst in preparing a benzylamine compound; the ionic iron (III) complex has the following structure:

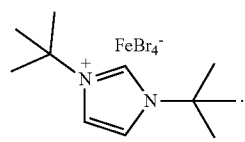

In the above technical solution, an aryl compound and an arylamine are used as starting materials in preparing the benzylamine compound in the presence an oxidizing agent.

In the above technical solution, the oxidizing agent is di-tert-butyl peroxide.

In the above technical solution, the method for preparing the benzylamine compound includes the following steps: mixing the catalyst, the arylamine, the oxidizing agent, the aryl compound, and reacting to obtain the benzylamine compound.

In the above technical solution, the aryl compound is a liquid and can be used as a reaction starting material and a solvent.

In the above technical solution, the reaction temperature is 80 to 150° C. and a reaction time is 15 to 60 hours;

In the above technical solution, after reaction is complete, the reaction solution is cooled to room temperature and purified by column chromatography to obtain the benzylamine compound. Preferably, a mixed solvent of ethyl acetate/petroleum ether with a volume ratio of 1:50 is used as an eluent in column chromatography.

In the above technical solution, based on moles, an amount of the oxidizing agent is 1 to 1.6 times of an amount of the arylamine, an amount of the catalyst is 5% to 20% of an amount of the arylamine.

In the preferable technical solution, the amount of the oxidizing agent is 1.5 times of the amount of the arylamine, the amount of the catalyst is 10% of the amount of the arylamine.

In the invention, the arylamine has the following structure:

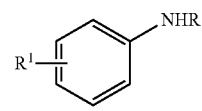

R is hydrogen or methyl; R$^1$ is cyano, nitro, trifluoromethyl or acetyl;

In the invention, the aryl compound has the following structure:

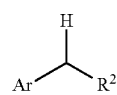

$R^2$ is hydrogen or methyl; Ar is one of phenyl, p-tert-butylphenyl, o-methylphenyl, mesitylphenyl, p-chlorophenyl, o-chlorophenyl, naphthyl and thienyl.

The above reaction for preparing the benzylamine compound be expressed as follows:

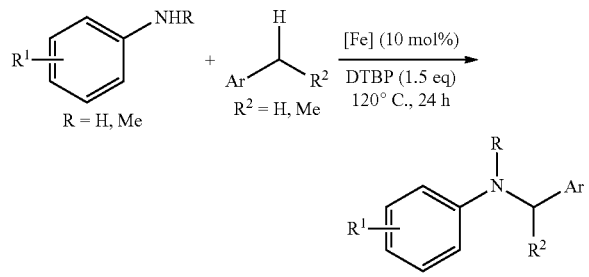

Beneficial Effect

Due to the application of the above technical solutions, the present invention has the following advantages compared with the prior art:

According to the invention, the iron (III) complex is used as a single component catalyst for the first time, so that the reaction between the toluene/ethylbenzene compound and the aromatic amine can be conducted, providing a new method for synthesizing the benzylamine compound. The iron (III) complex used in the present invention is a solid compound with definite structure and air stability, and has the characteristics of being low cost and easy to synthesize, green and environmentally friendly, and is beneficial to large-scale industrial synthesis applications.

The preparation method disclosed in the present invention has a wide range of applications, not only for toluene compounds containing primary carbon-hydrogen bonds in the benzyl position, but also for ethylbenzene compounds containing secondary carbon-hydrogen bonds in the benzyl position. The applicability of the substrate is improved; in particular, it solves that the existing method can only be applied to the compound containing the secondary carbon-hydrogen bond in the benzylic position, and is not applicable to the compound containing the primary carbon-hydrogen bond in the benzyl position.

EMBODIMENTS OF THE INVENTION

The present invention will be further described in combination with the following embodiments:

Example 1 Synthesis of Ionic Iron Complex Containing 1,3-di-tert-butylimidazole Cation (Molecular Formula [($^t$BuNCHCHN$^t$Bu)CH] [FeBr$_4$])

1, 3-Di-tert-butylimidazole bromide (0.26 g, 1.0 mmol) was added into the tetrahydrofuran solution of ferric tribromide (0.27 g, 0.9 mmol), reacting at 60° C. for 24 h. When the reaction was complete, the solvent was removed under vacuum, washed with hexane, dried, extracted with tetrahydrofuran, and centrifuged to collect the supernatant. Hexane was added to the supernatant to precipitate to obtain a red-brown crystal at room temperature, a yield of 89%.

Elemental Analysis

TABLE 1

| | C: (%) | H: (%) | N: (%) |
|---|---|---|---|
| Theoretical value | 23.73 | 3.80 | 5.03 |
| Actual value | 23.88 | 3.89 | 5.14 |

The complex [($^t$BuNCHCHN$^t$Bu)CH][FeBr$_4$] existed in the form of ion pairs, where [FeBr$_4$]$^-$ was characterized by Raman spectroscopy and it was found to have a characteristic peak at 204 cm$^{-1}$.

The cationic part of the complex, [($^t$BuNCHCHN$^t$Bu)CH]$^+$, was characterized by mass spectrometry and found to have a molecular ion peak at 181.1699. The theoretic molecular ion peak is at 181.1699. The measured results are consistent with the theoretic value.

It was confirmed that the obtained compound was the target compound, and the chemical structural formula is as follows:

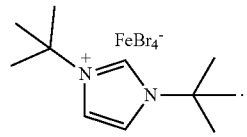

Example 2 [($^t$BuNCHCHN$^t$Bu)CH][FeBr$_4$] Catalyzed Reaction of p-cyanoaniline and Toluene In a reaction bottle, p-cyanoaniline (59 mg, 0.5 mmol), catalyst (28 mg, 0.05 mmol), di-tert-butyl peroxide (138 μL, 0.75 mmol), and toluene (7 mL) were added sequentially. The reaction was carried out at 120° C. for 24 hours. After the reaction was complete, the reaction mixture was cooled to room temperature. The product was purified by column chromatography eluting with ethyl acetate/petroleum ether with a volume ratio of 1:50, a yield of 88%.

When iron bromide (10 mol %) was used as the catalyst, the yield was only 8%. When tert-butyl hydroperoxide (1.5 times) was used as the oxidizing agent, the yield was only 22%.

The product was dissolved in CDCl$_3$ (ca. 0.4 mL), sealed, and characterized on a Unity Inova-400 NMR apparatus at room temperature: $^1$H NMR (400 MHz, CDCl$_3$, TMS): 7.38-7.28 (m, 7H), 6.58-6.55 (m, 2H), 4.73 (s, 1H), 4.35 (s, 2H) ppm.

Example 3 [($^t$BuNCHCHN$^t$Bu)CH][FeBr$_4$] Catalyzed Reaction of p-cyanoaniline and p-tert-butyltoluene In a reaction bottle, p-cyanoaniline (59 mg, 0.5 mmol), catalyst (14 mg, 0.025 mmol), di-tert-butyl peroxide (138 μL, 0.75 mmol), and p-tert-butyltoluene (7 mL) were added sequentially. The reaction was carried out at 80° C. for 60 hours. After the reaction was completed, the reaction mixture was is cooled to room temperature. The product was purified by column chromatography eluting with ethyl acetate/petroleum ether with a volume ratio of 1:50, a yield of 86%.

The product was dissolved in CDCl$_3$ (ca. 0.4 mL), sealed, and characterized on a Unity Inova-400 NMR apparatus at room temperature: $^1$H NMR (400 MHz, CDCl$_3$, TMS): 7.45

(m, 4H), 7.32 (d, J=7.9 Hz, 2H), 6.69-6.60 (m, 2H), 4.65 (s, 1H), 4.39 (s, 2H), 1.38 (s, 9H) ppm.

Example 4 [($^t$BuNCHCHN$^t$Bu)CH][FeBr$_4$] Catalyzed Reaction of p-cyanoaniline and o-xylene In a reaction bottle, p-cyanoaniline (59 mg, 0.5 mmol), catalyst (14 mg, 0.025 mmol), di-tert-butyl peroxide (138 μL, 0.75 mmol), and o-xylene (7 mL) were added sequentially. The reaction was carried out at 90° C. for 52 hours. After the reaction was completed, the reaction mixture cooled to room temperature. The product was purified by column chromatography eluting with ethyl acetate/petroleum ether with a volume ratio of 1:30, a yield of 83%.

The product was dissolved in CDCl$_3$ (ca. 0.4 mL), sealed, and characterized on a Unity Inova-400 NMR apparatus at room temperature: $^1$H NMR (400 MHz, CDCl$_3$, TMS): 7.50-7.45 (m, 2H), 7.35-7.21 (m, 4H), 6.68-6.61 (m, 2H), 4.57 (s, 1H), 4.37 (d, J=4.7 Hz, 2H), 2.42 (s, 3H) ppm.

Example 5 [($^t$BuNCHCHN$^t$Bu)CH][FeBr$_4$] Catalyzed Reaction of p-cyanoaniline and Mesitylene In a reaction bottle, adding p-cyanoaniline (59 mg, 0.5 mmol), catalyst (28 mg, 0.05 mmol), di-tert-butyl peroxide (92 μL, 0.5 mmol), and mesitylene (7 mL) were added sequentially. The reaction was carried out at 100° C. for 40 hours. After the reaction was completed, the action mixture was cooled to room temperature. The product was purified by column chromatography eluting with ethyl acetate/petroleum ether with a volume ratio of 1:10, a yield of 84%.

The product was dissolved in CDCl$_3$ (ca. 0.4 mL), sealed, and characterized on a Unity Inova-400 NMR apparatus at room temperature: $^1$H NMR (400 MHz, CDCl$_3$, TMS): 7.52-7.39 (m, 2H), 7.01 (s, 3H), 6.74-6.58 (m, 2H), 4.75 (s, 1H), 4.35 (d, J=5.1 Hz, 2H), 2.38 (s, 6H) ppm.

Example 6 [($^t$BuNCHCHN$^t$Bu)CH][FeBr$_4$] Catalyzed Reaction of p-cyanoaniline and p-chlorotoluene In a reaction bottle, p-cyanoaniline (59 mg, 0.5 mmol), catalyst (42 mg, 0.075 mmol), di-tert-butyl peroxide (138 μL, 0.75 mmol), and p-chlorotoluene (7 mL) were added sequentially. The reaction was carried out at 110° C. for 32 hours. After the reaction was completed, the reaction mixture was cooled to room temperature. The product was purified by column chromatography eluting with ethyl acetate/petroleum ether with a volume ratio of 1:50, a yield of 80%.

The product was dissolved in CDCl$_3$ (ca. 0.4 mL), sealed, and characterized on a Unity Inova-400 NMR apparatus at room temperature: $^1$H NMR (400 MHz, CDCl$_3$, TMS): 7.51-7.46 (m, 2H), 7.43-7.39 (m, 2H), 7.22 (d, J=8.4 Hz, 2H), 6.61-6.56 (m, 2H), 4.77 (s, 1H), 4.36 (s, 2H) ppm.

Example 7 [($^t$BuNCHCHN$^t$Bu)CH][FeBr$_4$] Catalyzed Reaction of p-cyanoaniline and o-chlorotoluene In a reaction bottle, p-cyanoaniline (59 mg, 0.5 mmol), catalyst (28 mg, 0.05 mmol), di-tert-butyl peroxide (138 μL, 0.75 mmol), and o-chlorotoluene (7 mL) were added sequentially. The reaction was carried out at 120° C. for 24 hours. After the reaction was completed, the reaction mixture was cooled to room temperature. The product was purified by column chromatography eluting with ethyl acetate/petroleum ether with a volume ratio of 1:10, a yield of 82%.

The product was dissolved in CDCl$_3$ (ca. 0.4 mL), sealed, and characterized on a Unity Inova-400 NMR apparatus at room temperature: $^1$H NMR (400 MHz, CDCl$_3$, TMS): 7.47-7.42 (m, 3H), 7.37 (d, J=4.2 Hz, 1H), 7.34-7.24 (m, 2H), 6.63 (d, J=8.8 Hz, 2H), 4.94 (s, 1H), 4.52 (d, J=5.9 Hz, 2H) ppm.

Example 8 [($^t$BuNCHCHN$^t$Bu)CH][FeBr$_4$] Catalyzed Reaction of p-cyanoaniline and 1-methylnaphthalene In a reaction bottle, p-cyanoaniline (59 mg, 0.5 mmol), catalyst (56 mg, 0.1 mmol), di-tert-butyl peroxide (138 μL, 0.75 mmol), and 1-methylnaphthalene (7 mL) were added sequentially. The reaction was carried out at 130° C. for 18 hours. After the reaction was completed, the reaction mixture was cooled to room temperature. The product was purified by column chromatography eluting with ethyl acetate/petroleum ether with a volume ratio of 1:10, a yield of 82%.

The product was dissolved in CDCl$_3$ (ca. 0.4 mL), sealed, and characterized on a Unity Inova-400 NMR apparatus at room temperature: 41 NMR (400 MHz, CDCl$_3$, TMS): 8.03 (dd, J=7.8, 1.9 Hz, 1H), 8.01-7.94 (m, 1H), 7.90 (d, J=7.6 Hz, 1H), 7.65-7.57 (m, 2H), 7.50 (dd, J=8.8, 5.4, 1.8 Hz, 4H), 6.73-6.62 (m, 2H), 4.81 (d, J=5.1 Hz, 2H), 4.68 (s, 1H) ppm.

Example 9 [($^t$BuNCHCHN$^t$Bu)CH][FeBr$_4$] Catalyzed Reaction of p-cyanoaniline and 2-methylthiophene In a reaction bottle, p-cyanoaniline (59 mg, 0.5 mmol), catalyst (56 mg, 0.1 mmol), di-tert-butyl peroxide (138 μL, 0.75 mmol), and 2-methylthiophene (7 mL) were added sequentially. The reaction was carried out at 130° C. for 38 hours. After the reaction was completed, the reaction mixture cooled to room temperature. The product was purified by column chromatography eluting with ethyl acetate/petroleum ether with a volume ratio of 1:10, a yield of 83%.

The product was dissolved in CDCl$_3$ (ca. 0.4 mL), sealed, and characterized on a Unity Inova-400 NMR apparatus at room temperature: $^1$H NMR (400 MHz, CDCl$_3$, TMS): 7.47 (d, J=8.8 Hz, 2H), 7.29 (dd, J=5.0, 1.2 Hz, 1H), 7.06 (d, J=0.7 Hz, 1H), 7.04 (d, J=5.0 Hz, 1H), 6.68 (d, J=8.8 Hz, 2H), 4.77 (s, 1H), 4.60 (d, J=5.5 Hz, 2H) ppm.

Example 10 [($^t$BuNCHCHN$^t$Bu)CH][FeBr$_4$] Catalyzed Reaction of p-trifluoromethylaniline and Toluene In a reaction bottle, p-trifluoromethylaniline (64 mg, 0.5 mmol), catalyst (28 mg, 0.05 mmol), di-tert-butyl peroxide (147 μL, 0.8 mmol), and toluene (7 mL) were added sequentially. The reaction was carried out at 140° C. for 16 hours. After the reaction was completed, the reaction mixture was cooled to room temperature. The product was purified by column chromatography eluting with ethyl acetate/petroleum ether with a volume ratio of 1:50, a yield of 75%.

The product was dissolved in CDCl$_3$ (ca. 0.4 mL), sealed, and characterized on a Unity Inova-400 NMR apparatus at room temperature: $^1$H NMR (400 MHz, CDCl$_3$, TMS): 7.38-7.26 (m, 7H), 6.58 (d, J=8.8 Hz, 2H), 4.31 (s, 3H) ppm.

Example 11 [(ᵗBuNCHCHNᵗBu)CH][FeBr₄] Catalyzed Reaction of p-acetylaniline and Toluene In a reaction bottle, p-acetylaniline (68 mg, 0.5 mmol), catalyst (28 mg, 0.05 mmol), di-tert-butyl peroxide (147 μL, 0.8 mmol), and toluene (7 mL) were added sequentially. The reaction was carried out at 150° C. for 15 hours. After the reaction was completed, the reaction mixture was cooled to room temperature. The product was purified by column chromatography eluting with ethyl acetate/petroleum ether with a volume ratio of 1:100, a yield of 74%.

The product was dissolved in CDCl₃ (ca. 0.4 mL), sealed, and characterized on a Unity Inova-400 NMR apparatus at room temperature: ¹H NMR (400 MHz, CDCl₃, TMS): 7.82-7.79 (m, 2H), 7.36-7.27 (m, 5H), 6.60-6.57 (m, 2H), 4.69 (s, 1H), 4.39 (d, J=4.8 Hz, 2H), 2.47 (s, 3H) ppm.

Example 12 [(ᵗBuNCHCHNᵗBu)CH][FeBr₄] Catalyzed Reaction of p-cyanoaniline and Ethylbenzene In a reaction bottle, p-cyanoaniline (59 mg, 0.5 mmol), catalyst (28 mg, 0.05 mmol), di-tert-butyl peroxide (147 μL, 0.8 mmol), and ethylbenzene (7 mL) were added sequentially. The reaction was carried out at 130° C. for 18 hours. After the reaction was completed, the reaction mixture was cooled to room temperature. The product was purified by column chromatography eluting with ethyl acetate/petroleum ether with a volume ratio of 1:5, a yield of 81%.

The product was dissolved in CDCl₃ (ca. 0.4 mL), sealed, and characterized on a Unity Inova-400 NMR apparatus at room temperature: ¹H NMR (400 MHz, CDCl₃, TMS): 7.34-7.28 (m, 6H), 7.26-7.21 (m, 1H), 6.48-6.45 (m, 2H), 4.70 (s, 1H), 4.51 (q, J=6.7 Hz, 1H), 1.53 (d, J=6.7 Hz, 3H) ppm.

Example 13 [(ᵗBuNCHCHNᵗBu)CH][FeBr₄] Catalyzed Reaction of p-nitroaniline and Ethylbenzene In a reaction bottle, p-nitroaniline (69 mg, 0.5 mmol), catalyst (28 mg, 0.05 mmol), di-tert-butyl peroxide (138 μL, 0.75 mmol), and ethylbenzene (7 mL) were added sequentially. The reaction was carried out at 140° C. for 16 hours. After the reaction was completed, it is cooled to room temperature. The product was purified by column chromatography eluting with ethyl acetate/petroleum ether with a volume ratio of 1:20, a yield of 80%.

The product was dissolved in CDCl₃ (ca. 0.4 mL), sealed, and characterized on a Unity Inova-400 NMR apparatus at room temperature: ¹H NMR (400 MHz, CDCl₃, TMS): 7.98-7.97 (m, 2H), 7.37-7.30 (m, 4H), 7.27-7.23 (m, 1H), 6.47-6.43 (m, 2H), 4.95 (d, J=4.8 Hz, 1H), 4.58 (q, J=6.4 Hz, 1H), 1.57 (d, J=6.8 Hz, 3H) ppm.

Example 14 [(ᵗBuNCHCHNᵗBu)CH][FeBr₄] Catalyzed Reaction of n-methyl-p-nitroaniline and Toluene In a reaction bottle, n-methyl-p-nitroaniline (76 mg, 0.5 mmol), catalyst (42 mg, 0.075 mmol), di-tert-butyl peroxide (138 μL, 0.75 mmol), and toluene (7 mL) were added sequentially. The reaction was carried out at 140° C. for 16 hours. After the reaction was completed, the reaction mixture was cooled to room temperature. The product was purified by column chromatography eluting with ethyl acetate/petroleum ether with a volume ratio of 1:10, a yield of 68%.

The product was dissolved in CDCl₃ (ca. 0.4 mL), sealed, and characterized on a Unity Inova-400 NMR apparatus at room temperature: ¹H NMR (400 MHz, CDCl₃, TMS): 8.14 (d, J=9.4 Hz, 2H), 7.39 (d, J=7.6 Hz, 3H), 7.22 (d, J=7.1 Hz, 2H), 6.71 (d, J=9.4 Hz, 2H), 4.73 (s, 2H), 3.24 (s, 3H) ppm.

Example 15 [(ᵗBuNCHCHNᵗBu)CH][FeBr₄] Catalyzed Reaction of n-methyl-p-cyanoaniline and Toluene In a reaction bottle, n-methyl-p-cyanoaniline (66 mg, 0.5 mmol), catalyst (56 mg, 0.1 mmol), di-tert-butyl peroxide (138 μL, 0.75 mmol), and toluene (7 mL) were added sequentially. The reaction was carried out at 130° C. for 18 hours. After the reaction was completed, the reaction mixture was cooled to room temperature. The product was purified by column chromatography eluting with ethyl acetate/petroleum ether with a volume ratio of 1:10, a yield of 75%.

The product was dissolved in CDCl₃ (ca. 0.4 mL), sealed, and characterized on a Unity Inova-400 NMR apparatus at room temperature: ¹H NMR (400 MHz, CDCl₃, TMS): 7.52-7.46 (m, 2H), 7.37 (dd, J=25.5, 3.8 Hz, 3H), 7.22 (d, J=7.3 Hz, 2H), 6.77-6.71 (m, 2H), 4.67 (s, 2H), 3.18 (s, 3H) ppm.

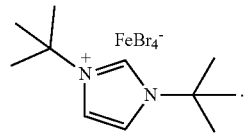

The invention claimed is:

1. A method for preparing a catalyst for preparing a benzylamine compound comprising:
   adding 1,3-di-tert-butylimidazole bromide into a tetrahydrofuran solution of ferric tribromide,
   reacting at 60° C. for 24 h,
   removing tetrahydrofuran under vacuum,
   washing with hexane,
   drying and extracting with tetrahydrofuran,
   centrifugating to collecting a supernatant, and
   adding hexane to the supernatant to precipitate the catalyst at room temperature as a red brown crystal,
   wherein the catalyst is an ionic iron (III) complex having the following structure: